United States Patent
Chapman et al.

(10) Patent No.: US 7,563,889 B1
(45) Date of Patent: Jul. 21, 2009

(54) 3,3,7,7,-TETRAKIS(DIFLUORAMINO)OCTA HYDRO-1,5-DIAZOCINIUM SALTS AND METHOD FOR MAKING THE SAME

(75) Inventors: Robert D. Chapman, Ridgecrest, CA (US); Thomas J. Groshens, Ridgecrest, CA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 525 days.

(21) Appl. No.: 11/010,058

(22) Filed: Dec. 10, 2004

(51) Int. Cl.
*C07D 245/00* (2006.01)
(52) U.S. Cl. ...................................... 540/470
(58) Field of Classification Search ........................ None
See application file for complete search history.

(56) References Cited

OTHER PUBLICATIONS

U.S. Appl. No. 11/010059, filed Dec. 2004, Chapman et al.*
Chapman et al. Difluoroamination of heterocyclic ketones: control of Microbasicity, Journal of Organic Chemistry, 1998, 63, 1566-1570.*
Chapman et al. Nitrolysis of a highly deactivated amide by protonitronium. Synthesis and structure of HNFX, Journal of Organic Chemistry, 1999, 64, 960-965.*

* cited by examiner

*Primary Examiner*—James O Wilson
*Assistant Examiner*—Noble Jarrell
(74) *Attorney, Agent, or Firm*—Charlene A. Haley; Brian F. Drazich

(57) ABSTRACT

3,3,7,7-Tetrakis(difluoramino)octahydro-1,5-diazocinium intermediate salts and method for making the salts, through difluoramination followed by N-denosylation or N-deprotection, which are valuable for use as precursor(s) to HNFX as well as to other members of the rare class of 3,3,7,7-tetrakis (difluoramino)octahydro-1,5-diazocines.

5 Claims, No Drawings

3,3,7,7,-TETRAKIS(DIFLUORAMINO)OCTAHYDRO-1,5-DIAZOCINIUM SALTS AND METHOD FOR MAKING THE SAME

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The present invention relates to 3,3,7,7-tetrakis(difluoramino)octahydro-1,5-diazocinium salts and method for making the same, and more specifically, a method of making the salts through difluoramination followed by N-denosylation or N-deprotection.

BACKGROUND OF THE INVENTION

Methodology for preparing a geminal-bis(difluoramino)-substituted nitrogenous heterocycle has been reported by Chapman et al. [*Journal of Organic Chemistry* 1998, 63, 1566-1570], who described the preparation of 3,3,7,7-tetrakis(difluoramino)octahydro-1,5-bis(4-nitrobenzenesulfonyl)-1,5-diazocine; this intermediate has been converted to the corresponding nitramine, 3,3,7,7-tetrakis(difluoramino)octahydro-1,5-dinitro-1,5-diazocine, given the acronym HNFX [Chapman et al., *Journal of Organic Chemistry* 1999, 64, 960-965]. Attempts have been made to convert 1,5-diacetyltetrahydro-1,5-diazocine-3,7(2H,6H)-dione to the corresponding 3,3,7,7-tetrakis(difluoramino)diazocine that led to facile addition of one difluoramine to one carbonyl site, but prolonged reaction to disrupt the stable transannular bridge which resulted only in degradation of the organic substrate, as reported by Chapman et al. ["Research in Energetic Compounds", September 1991, Fluorochem Inc., Azusa, Calif., Report ONR-7-1; final report to the Office of Naval Research (Arlington, Va.) on Contract N00014-88-C-0536; described by Baum, K. et al. "Novel Approaches to the Synthesis of Fluorodinitromethane and Fluorodinitroethanol", August 1993, Fluorochem Inc., Azusa, Calif., Report NRO-1-1; *Chemical Abstracts* 1995, 123, 339081r; NTIS Accession Number AD-A269158]. Using nitro as an alternative N-protecting group allowed further progress of the sequence to HNFX. Thus, nitrolysis of 3,7-diacetyl-5-(difluoramino)-9-oxa-3,7-diazabicyclo[3.3.1]nonan-1-ol produced an unprecedented nitrate ester of a hemiacetal, 5-(difluoramino)-3,7-dinitro-9-oxa-3,7-diazabicyclo[3.3.1]non-1-yl nitrate, which underwent slow spontaneous elimination of $NO_2$ after workup. Difluoramination of the nitro-protected diazocine under conventional conditions allowed the formation of desired nitramine, but the yield was quite poor (~1% in the last step) due to the known instability of nitramines in strong non-nitrating acids.

A 3,3,7,7-tetrakis(difluoramino)octahydro-1,5-diazocine was desired as a potential precursor to 3,3,7,7-tetrakis(difluoramino)octahydro-1,5-dinitro-1,5-diazocine (HNFX), the first example of a new class of compounds predicted to be potentially superior explosives or solid propellant oxidizers: gem-bis(difluoramino)-substituted heterocyclic nitramines. vic-Bis(difluoramino)-substituted primary nitramines and N-alkyl-N-(difluoraminomethyl)nitramines have been reported in prior literature. However, the synthesis of gem-bis(difluoramino) alkanes has required strongly acidic conditions, such as anhydrous sulfuric acid, difluorosulfamic acid, or fluorosulfonic acid, with which most nitramines are incompatible. In the first synthesis of HNFX, for example, the use of 5-(difluoramino)-3,7-dinitro-9-oxa-3,7-diazabicyclo[3.3.1]nonan-1-ol in a typical difluoramination reaction (difluoramine-difluorosulfamic acid-sulfuric acid) produced HNFX in only ~1% yield. Therefore, the N-nitro component is preferably incorporated after difluoramination to produce gem-bis(difluoramino)alkyl components. A dilemma encountered in the preparation of a β,β-bis(difluoramino)-substituted heterocycle, such as a 3,3,7,7-tetrakis(difluoramino)octahydro-1,5-diazocine, is that the nitrogen in most 1,3-diaminoacetone derivatives would be more basic than the ketone carbonyl (and oxygen in hemiaminal intermediates), thereby deactivating difluoramination via difluoramino-carbocations, unless the nitrogen is protected with a sufficiently electronegative protecting group to favorably affect this basicity [Chapman et al., *Journal of Organic Chemistry* 1998, 63, 1566-1570].

There exists a need in the art for 3,3,7,7-tetrakis(difluoramino)octahydro-1,5-diazocinium salts for use as precursors to HNFX as well as to other members of the rare class of 3,3,7,7-tetrakis(difluoramino)octahydro-1,5-diazocines.

SUMMARY OF THE INVENTION

The present invention relates to a method for making 3,3,7,7-tetrakis(difluoramino)octahydro-1,5-diazocinium salt (C) comprising: providing an effective amount of a tetrahydro-1,5-disulfonyl-1,5-diazocine-3,7(2H,6H)-dione (A); subjecting the dione (A) to difluoramination, with suitable protection of ring nitrogens (positions 1 and 5) within the dione to produce a 3,3,7,7-tetrakis(difluoramino)octahydro-1,5-disulfonyl-1,5-diazocine intermediate (B); and subjecting an effective amount of 3,3,7,7-tetrakis(difluoramino)octahydro-1,5-disulfonyl-1,5-diazocine intermediate (B) to protolytic N-deprotection by adding a superacid, generating deprotected 3,3,7,7-tetrakis(difluoramino)octahydro-1,5-diazocinium salt (C).

It is to be understood that the foregoing general description and the following detailed description are exemplary and explanatory only and are not to be viewed as being restrictive of the present invention, as claimed. Further advantages of this invention will be apparent after a review of the following detailed description of the disclosed embodiments and in the appended claims.

DETAILED DESCRIPTION OF THE INVENTION

The present invention relates to 3,3,7,7-tetrakis(difluoramino)octahydro-1,5-diazocinium salts (C) and the method for making the salts. A method of making a 3,3,7,7-tetrakis(difluoramino)octahydro-1,5-diazocinium salt (C) comprising: providing an effective amount of a tetrahydro-1,5-disulfonyl-1,5-diazocine-3,7(2H,6H)-dione (A); subjecting the dione (A) to difluoramination, with suitable protection of ring nitrogens (positions 1 and 5) within the dione to produce a 3,3,7,7-tetrakis(difluoramino)octahydro-1,5-disulfonyl-1,5-diazocine intermediate (B); and subjecting an effective amount of 3,3,7,7-tetrakis(difluoramino)octahydro-1,5-disulfonyl-1,5-diazocine intermediate (B) to protolytic N-deprotection by adding a superacid, generating deprotected 3,3,7,7-tetrakis(difluoramino)octahydro-1,5-diazocinium salt (C) having the formula:

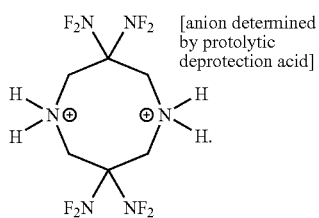

An effective amount of a suitably N-protected tetrahydro-1,5-disulfonyl-1,5-diazocine-3,7(2H,6H)-dione (A) is an amount equal to or less than ¼ of the number of moles of difluoramine added. An effective amount of the 3,3,7,7-tetrakis(difluoramino)octahydro-1,5-disulfonyl-1,5-diazocine intermediate (B) is what is formed from the first reaction of (A) and difluoramine. The tetrahydro-1,5-disulfonyl-1,5-diazocine-3,7(2H,6H)-dione (A) comprises at least one of the class of tetrahydro-1,5-diazocine-3,7(2H,6H)-diones,

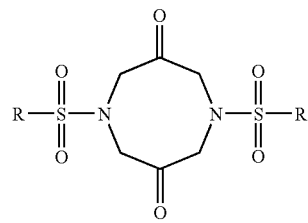

wherein (A) is substituted on the ring nitrogens (positions 1 and 5) by electron-withdrawing sulfonyl substituents $SO_2R$ that lower the basicity of the ring nitrogens below that of the ketone carbonyl oxygens; and wherein R comprises at least one of halo, polyhaloalkyl, polyhaloaryl, any regioisomer of cyanoaryl, polycyanoaryl, any regioisomer of nitroaryl, polynitroaryl, and heteroaryl. The 3,3,7,7-tetrakis(difluoramino)octahydro-1,5-disulfonyl-1,5-diazocine intermediate (B) has the formula

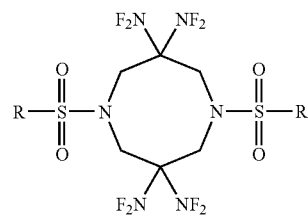

wherein R on the 3,3,7,7-tetrakis(difluoramino)octahydro-1,5-disulfonyl-1,5-diazocine intermediate (B) comprises at least one of halo, polyhaloalkyl, polyhaloaryl, any regioisomer of cyanoaryl, polycyanoaryl, any regioisomer of nitroaryl, polynitroaryl, and heteroaryl.

The difluoramination process includes the use of difluoramine and difluorosulfamic acid in sulfuric acid. In one embodiment, the superacid disrupts further difluoramination, decomposes deleterious partially difluoraminated intermediates, and continues N-deprotection. The superacid comprises at least one of trifluoromethanesulfonic acid, any suitable difluoraminating acid including difluorosulfamic acid-sulfuric acid mixtures, mixtures of trifluoromethanesulfonic acid with any suitable difluoraminating acid including difluorosulfamic acid-sulfuric acid, fluorosulfonic acid, any perfluoroalkanesulfonic acid, any perfluoroarenesulfonic acid, any acid with a Hammett acidity constant ($H_0$) less than that of sulfinuric acid (approximately −11), and any of these acids in the presence of appropriate good Lewis acid additives including antimony pentafluoride or bismuth trifluoromethanesulfonate.

In another embodiment, the 3,3,7,7-tetrakis(difluoramino)octahydro-1,5-diazocinium salt (C) produced by the method above has the formula

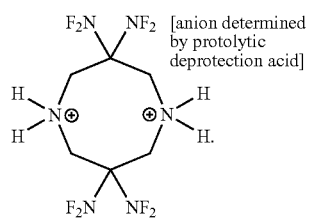

In a further embodiment, the 3,3,7,7-tetrakis(difluoramino)octahydro-1,5-diazocinium salt (C) comprises, an effective amount of tetrahydro-1,5-disulfonyl-1,5-diazocine-3,7(2H,6H)-dione (A) subjected to difluoramination to produce 3,3,7,7-tetrakis(difluoramino)octahydro-1,5-disulfonyl-1,5-diazocine intermediate (B), wherein R on the 3,3,7,7-tetrakis(difluoramino)octahydro-1,5-disulfonyl-1,5-diazocine intermediate (B) comprises at least one of halo, polyhaloalkyl, polyhaloaryl, any regioisomer of cyanoaryl, polycyanoaryl, any regioisomer of nitroaryl, polynitroaryl, and heteroaryl; and

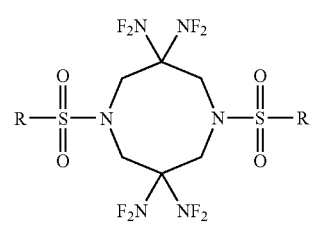

wherein an effective amount of the 3,3,7,7-tetrakis(difluoramino)octahydro-1,5-disulfonyl-1,5-diazocine intermediate (B) is subjected to protolytic N-deprotection to deprotected 3,3,7,7-tetrakis(difluoramino)octahydro-1,5-diazocinium salt (C) having the formula

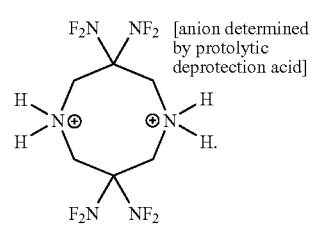

The tetrahydro-1,5-disulfonyl-1,5-diazocine-3,7(2H,6H)-dione (A) in this embodiment also includes at least one of the class of tetrahydro-1,5-diazocine-3,7(2H,6H)-diones:

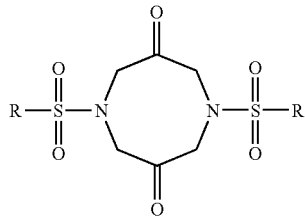

(A)

wherein (A) is substituted on the ring nitrogens (positions 1 and 5) by electron-withdrawing sulfonyl substituents $SO_2R$ that lower the basicity of the ring nitrogens below that of the ketone carbonyl oxygens; and wherein R comprises at least one of halo, polyhaloalkyl, polyhaloaryl, any regioisomer of cyanoaryl, polycyanoaryl, any regioisomer of nitroaryl, polynitroaryl, and heteroaryl. Furthermore, difluoramination in this embodiment includes the use of difluoramine and difluorosulfamic acid in sulfuric acid. Additionally, the superacid comprises at least one of trifluoromethanesulfonic acid, any suitable difluoraminating acid including difluorosulfamic acid-sulfuric acid mixtures, mixtures of trifluoromethane-sulfonic acid with any suitable difluoraminating acid including difluorosulfamic acid-sulfuric acid, fluorosulfonic acid, any perfluoroalkanesulfonic acid, any perfluoroarenesulfonic acid, any acid with a Hammett acidity constant ($H_0$) less than that of sulfuric acid (approximately −11), and any of these acids in the presence of appropriate good Lewis acid additives including antimony pentafluoride or bismuth trifluoromethanesulfonate.

Another embodiment includes the 3,3,7,7-tetrakis(difluoramino)octahydro-1,5-diazocinium salt (C) having the formula

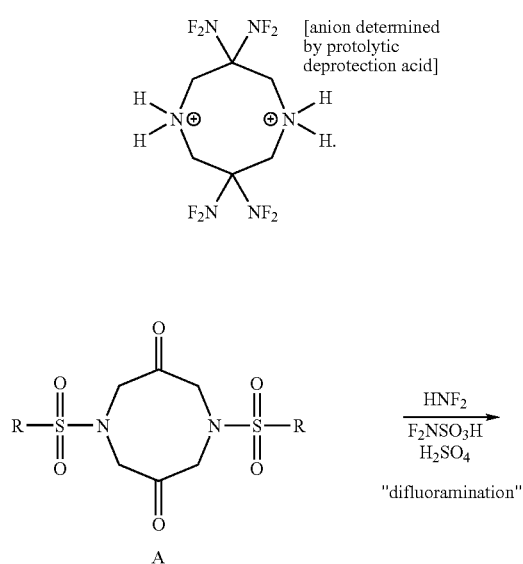

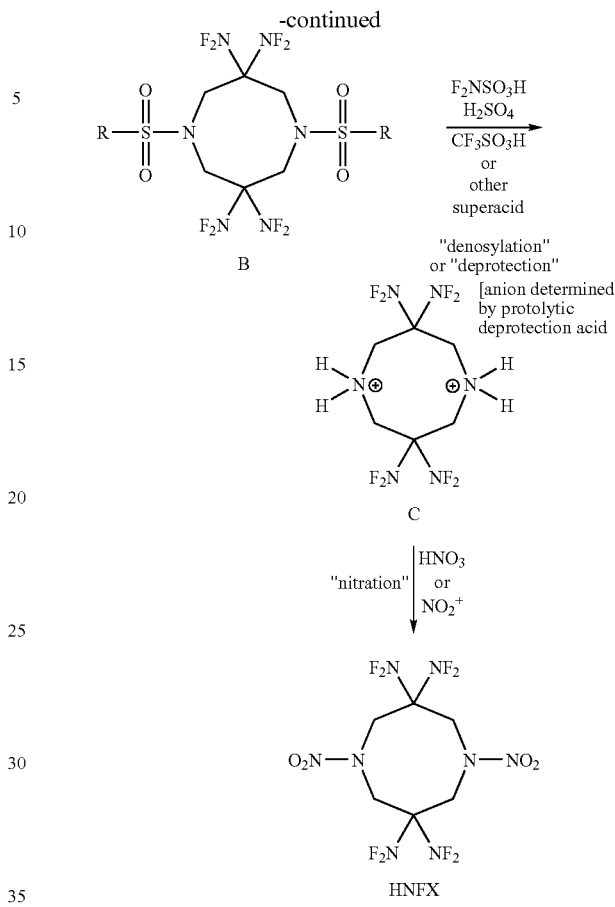

R = electron-withdrawing substituent, such as halo, haloalkyl, polyhaloalkyl, any regioisomer of haloaryl, polyhaloaryl, any regioisomer of cyanoarenyl, polycyanoaryl, any regioisomer of nitroaryl, or polynitroaryl The above flow chart demonstrates the conversion of a tetrahydro-1,5-diazocine-3,7(2H,6H)-dione, such as, for example, a tetrahydro-1,5-bis(4-nitrobenzenesulfonyl)-1,5-diazocine-3,7(2H,6H)-dione (A where R=4-nitrophenyl), a material commercially available from Fluorochem Inc., Azusa, California, to 3,3,7,7-tetrakis(difluoramino)octahydro-1,5-dinitro-1,5-diazocine (HNFX) in one pot without isolation of any other intermediates. An important aspect of the present invention is the nature of the substitution on the diazocines' nitrogen atoms. The nitrogen atoms of diazocine intermediates and precursors must be suitably substituted ("protected") during the process of difluoramination to allow this process to proceed to geminal-bis(difluoramino)alkylene derivatives. Without suitable protection of proximate nitrogens (especially those separated from reacting carbonyl sites by a short bridge, such as methylene), the process of difluoramination of ketone intermediates does not proceed to geminal-bis(difluoramino)alkylene derivatives but only to mono(difluoramino)alkylene derivatives or not at all.

The nitrogen-protecting groups chosen for the diazocine intermediates and precursors are certain sulfonyl substituents. The particular sulfonyl substituents are chosen from a group that favorably affects the basicity of the diazocine nitrogens to make them less basic than the oxygen sites in the diazocine intermediates, in order to allow difluoramination of the carbonyl oxygens to proceed to geminal-bis(difluoramino)alkylene derivatives. Tetrahydro-1,5-diazocine-3,7(2H,6H)-diones suitable for conversion to 3,3,7,7-tetrakis(difluoramino)octahydro-1,5-diazocines are substituted on the ring nitrogens (positions 1 and 5) by electron-withdrawing sulfonyl substituents. The substituent causes the nitrogens to have acid dissociation constants ($pK_a$) of the (protonated) conjugate acid forms of the nitrogen sites that are less than that of a ketone carbonyl group, which is typically about –7. These substituents may include alkanesulfonyl or halosulfonyl substituents as well as arenesulfonyl substituents. Suitable benzenesulfonyl substituents must have electronwithdrawing substituents on the phenyl rings.

An example of a suitable electron-withdrawing substituent on phenyl rings is the nitro ($NO_2$) group, as employed in Examples below. Any single or multiple electron-withdrawing substituent(s) that collectively lower(s) the basicity of arenesulfonyl-protected nitrogens below that of the oxygen in corresponding tetrahydro-1,5-diazocine-3,7(2H,6H)-diones is (are) suitable. The quantitative effect of numerous substituents on basicity is well known in the chemical community, as reviewed by Hansch et al. [*Chemical Reviews* 1991, 91, 165]. Likewise, alkanesulfonyl protecting groups may be electronegatively substituted to impart the same property on the protected nitrogens. In general, the sulfonyl substituent must have an inductive substituent constant (symbolized by $\sigma_I$ or F according to the literature of Hansch et al., op. cit.) of a value greater than that of unsubstituted benzenesulfonyl, approximately 0.58. Thus, 4-nitrobenzenesulfonyl ("nosyl"), with $\sigma_I$=0.61, is suitable and successful at allowing difluoramination of the corresponding protected tetrahydro-1,5-diazocine-3,7(2H,6H)-diones. Nosyl is the model N-protecting group employed in our successful Examples below.

In the new conversion process of the present invention, the tetrahydro-1,5-bis(4-nitrobenzenesulfonyl)-1,5-diazocine-3,7(2H,6H)-dione ("dione" A where R=4-nitrophenyl) is subjected to difluoramination with difluoramine and difluorosulfamic acid in sulfuric acid, similar to the procedure previously reported by Chapman et al. [*Journal of Organic Chemistry* 1998, 61, 1566] but with modifications in conditions in order for the reaction to proceed faster and/or with higher conversion efficiency. The progress of difluoramination is monitored spectroscopically until competitive protolytic N-denosylation of the contained intermediate, 3,3,7,7-tetrakis-(difluoramino)octahydro-1,5-bis(4-nitrobenzenesulfonyl)-1,5-diazocine (B), ensues. Protolytic N-denosylation replaces a nosyl N-protecting group with protons, forming the corresponding protonated amine or ammonium derivative. Competitive protolytic denosylation by the difluoramination acid mixture prevents further difluoramination of the carbonyl group(s) to geminal-bis(difluoramino)alkylene group(s).

When competitive protolytic N-denosylation commences during difluoramination, a "superacid," such as trifluoromethanesulfonic acid, is added, which disrupts further difluoramination, decomposes deleterious partially difluoraminated intermediates, and continues N-denosylation, generating deprotected 3,3,7,7-tetrakis(difluoramino)octahydro-1,5-diazocinium (C) salt(s). The contained deprotected intermediate salt (C) is then readily nitrated by simple addition of nitric acid. A preparation of HNFX reported by Chapman et al. [*Journal of Organic Chemistry* 1999, 62, 960] utilizes a mixture of trifluoromethanesulfonic acid plus nitric acid in order to effect nitrolytic denosylation.

The present invention is superior in that the reported mixture of nitric acid plus trifluoromethanesulfonic acid involves complex chemical equilibria, with nitronium trifluoromethanesulfonate, protonitronium ($NO_2H^{2+}$) trifluoromethanesulfonate, and hydronium ($H_3O^+$) trifluoromethanesulfonate species also being present. Such nitrolytic denosylation is effective only in a narrow range of concentratios of the various reactants (diazocine reactant, nitric acid, and trifluoromethanesulfonic acid), and the process is not economical, as the organic reactant[3,3,7,7-tetrakis(difluoramino)octahydro-1,5-bis(4-nitrobenzenesulfonyl)-1,5-diazocine B] is soluble to the extent of only approximately 0.3 weight percent in the nitrolyzing mixture. In contrast, protolytic denosylation by a superacid, being trifluoromethanesulfonic acid (including its mixtures with the difluoraminating acid mixture) in the present invention, is carried out with a concentration in the range of 5-10 weight percent organic reactant. Also, the intermediate reactant, 3,3,7,7-tetrakis(difluoramino)octahydro-1,5-bis(4-nitrobenzenesulfonyl)-1,5-diazocine (B), need not be isolated for the deprotection reaction, which isolation had proven to be problematic in the process of preparing HNFX by the literature procedures. Thus, the present invention is more efficient in terms of use of reagents and reaction time. Also, the yield of isolated HNFX remains comparable to that produced in the discretely stepwise reactions in procedures previously reported.

Protolytic denosylation, newly demonstrated here, is a novel N-deprotection process in that conventional wisdom in the art of chemistry purports that nosylamides (nosyl-protected amines) are stable to strong acids, as reviewed by Greene and Wuts ["Protective Groups in Organic Synthesis," 3$^{rd}$ ed., John Wiley & Sons, 1999; pages 609-610]. The four β-difluoramino substituents of a diazocine such as 3,3,7,7-tetrakis(difluoramino)octahydro-1,5-bis(4-nitrobenzenesulfonyl)-1,5-diazocine (B) further deactivate the nosyl leaving group toward electrophilic displacement, due to their inductive effect and steric hindrance toward the nosylamide components of B. However, the present invention employs "super-strong" acids ("superacids") in order to effectively protolytically denosylate the nosylamide intermediates used here, such as 3,3,7,7-tetrakis(difluoramino)octahydro-1,5-bis(4-nitrobenzenesulfonyl)-1,5-diazocine (B). In the case of nosyldiazocines, the protolytically denosylated diazocine is a diazocinium ion; its counteranion(s) is (are) determined by the acid mixture used for protolysis. The denosylated diazocine formed in the present invention is an unprecedented 3,3,7,7-tetrakis(difluoramino)octahydro-1,5-diazocinium salt (C); its counteranions are species including trifluoromethanesulfonate, fluorosulfonate, sulfate, and/or bisulfate. Superacids that are suitable for protolytically denosylating nosylamides should be stronger than sulfuric acid, which has a Hammett acidity function ($H_0$) of approximately –11. Superacids and their preparation have been reviewed by Olah et al. ["Superacids," John Wiley & Sons, 1985].

Resulting protolytically deprotected diazocines (diazocinium salts) are then readily nitrated by simple addition of nitric acid. In another embodiment, the nitric acid may combine with the superacid(s) used as a protolytic denosylation reagent, but the product of such combination is likely to be a nitronium salt that is also capable of nitrating the generated diazocinium ion intermediate, nitration of which forms desired HNFX. The following experiments are exemplary and explanatory only and are not to be viewed as being restrictive of the present invention, as claimed.

EXPERIMENTAL RESULTS

Example 1

One-Pot Denosylation/Nitration

Dry distilled trifluoromethanesulfonic acid (80 g, 0.53 mole) was weighed out in a 100-mL round-bottom flask, which was then fitted with a bubbler to keep the contents under a dry nitrogen atmosphere. The flask was cooled with a liquid nitrogen bath long enough to freeze the acid. A stirbar and 4.01 g (5.86 mmol) of purified 3,3,7,7-tetrakis(difluoramino)octahydro-1,5-bis(4-nitrobenzenesulfonyl)-1,5-diazocine (B) were added on top of the solidified acid, and the contents were allowed to warm to room temperature, with stirring, to form a light tan slurry. The contents were stirred under nitrogen at room temperature for 40 h. (The sample was a homogeneous single phase after stirring overnight, approximately 14 h.) The flask was placed in an oil bath and maintained at 40° C. for an additional 12 days. The reaction was monitored periodically by removing aliquots (for $^1$H and $^{19}$F NMR analysis) which were subsequently returned to the flask. The reaction flask was cooled to 0° C. in an ice-water bath, and 6.4 g of 98-100% nitric acid (0.10 mole=19 mole % nitric acid relative to triflic acid) was slowly added with stirring over a 5-min period. The resulting thick light-brown slurry was allowed to warm to room temperature and stir for one hour. The reaction mixture was slowly poured over 500 mL of ice with mixing. The pH of the mixture was adjusted to 5 with saturated aqueous sodium carbonate solution. (In some reactions, HNFX was collected from the acidic solution by filtration and then washed with aqueous sodium carbonate and water to remove the excess acid, without any significant effect on the yield.) The precipitated HNFX was collected on a 60-mL medium-porosity fritted glass funnel and washed with an additional 250 mL of distilled water. The frit and product were dried in a vacuum desiccator overnight. The crude yield was 1.89 g product that was 94 wt % HNFX with some trifluoromethanesulfonate salt, nitrobenzenesulfonyl fluoride, and mononosyldiazocine impurities. The corrected calculated yield of HNFX was 75%.

Example 2

One-Pot Difluoramination/Denosylation

To a 4-liter jacketed cylindrical flask (the "reactor"), which had been previously purged with nitrogen for 1 hour, was added 610 mL of fuming sulfinuric acid (20% $SO_3$) and 1200 mL of trichlorofluoromethane ("Freon"). The flask was equipped with a mechanical stirrer, a Dewar-style reflux condenser (containing dry ice, acetone, and a refrigerated cold-finger), and an inert-oil-filled bubbler. The fuming sulfuric acid-Freon mixture was cooled with a chilled circulating bath set to −20° C. To a separate 5-liter, 3 neck, round-bottom flask was added 3 liters of aqueous N,N-difluorourea solution containing 8.2 moles difluorourea. Gaseous difluoramine ($HNF_2$) was generated from the difluorourea solution by acidic hydrolysis with sulfuric acid, as described by Parker and Freeman [*Inorganic Syntheses* 1970, 12, 307], and absorbed into the cooled fuming sulfuric acid. When $HNF_2$ generation was complete, tetrahydro-1,5-bis(4-nitrobenzenesulfonyl)-1,5-diazocine-3,7(2H,6H)-dione A (150 g, 0.293 mole) was added to the fuming sulfuric acid—Freon mixture, the flask was sealed and its temperature was set to −17° C., and the mixture was stirred.

On the second day, the temperature was raised to −10° C. On the 7h day, the temperature was raised to −8° C. On the 9$^{th}$ day, the difluoramination reaction was proceeding slowly (according to NMR analysis); another 62 ml of fuming sulfuric acid (20% $SO_3$) was added along with 250 mL Freon, and the reaction continued stirring at −8° C. On the 14$^{th}$ day, the reaction temperature was increased to 0° C. On the 16$^{th}$ day, NMR analysis showed that the reaction had progressed and then stopped; another 57 mL of fuming sulfuric acid (20% $SO_3$) was added over 1½ hour along with another 350 mL of Freon, and the reaction was stirred at 1° C.

On the 17$^{th}$ day, NMR analysis showed that difluoramination had converted tetrahydro-1,5-bis(4-nitrobenzenesulfonyl)-1,5-diazocine-3,7(2H,6H)-dione (A) to 64 mole % 3,3,7,7-tetrakis-(difluoramino)octahydro-1,5-bis(4-nitrobenzenesulfonyl)-1,5-diazocine (B) by the time competitive denosylation by the difluoramination acid mixture commenced. Distilled trifluoromethanesulfonic acid (1000 mL) was added over 2 h, and the mixture was heated to 22° C. (with stirring) and left stirring, effecting protolytic denosylation of the 3,3,7,7-tetrakis(difluoramino)octahydro-1,5-bis(4-nitrobenzenesulfonyl)-1,5-diazocine (B).

Example 3

One-Pot Difluoramination/Denosylation/Nitration

To a 4-liter jacketed cylindrical flask (the "reactor"), which had been previously purged with nitrogen for 1 hour, was added 400 mL of fuming sulfuric acid (30% $SO_3$) and 800 mL of trichlorofluoromethane ("Freon"). The flask was equipped with a mechanical stirrer, a Dewar-style reflux condenser (containing dry ice, acetone, and a refrigerated cold-finger), and an inert-oil-filled bubbler. The fuming sulfuric acid-Freon mixture was cooled with a chilled circulating bath. To a separate 5-liter, 3 neck, round-bottom flask was added 3 liters of aqueous N,N-difluorourea solution containing 8.5 moles difluorourea. When the difluoramination reactor temperature reached +9° C., gaseous difluoramine ($HNF_2$) was generated from the difluorourea solution by acidic hydrolysis with sulfuric acid, as described by Parker and Freeman [*Inorganic Syntheses* 1970, 12, 307], and absorbed into the cooled fuming sulfuric acid. When $HNF_2$ generation was complete, and the reactor temperature had cooled to approximately −8° C., tetrahydro-1,5-bis(4-nitrobenzenesulfonyl)-1,5-diazocine-3,7(2H,6H)-dione A (150 g, 0.293 mole) was added to the fuming sulfinuric acid—Freon mixture, the reactor flask was sealed and cooled further to −15° C., and the mixture was stirred.

On the 15$^{th}$ day of reaction, 62 mL of fuming sulfuric acid (20% $SO_3$) was added over 30 min, the reaction flask was sealed, and the contents were stirred at −14° C. for five days. At the end of the five days, another 62 mL of fuming sulfuric acid (20% $SO_3$) was added over 45 min, the temperature was raised to −10° C., and the contents were stirred for two days. At the end of the two days, the temperature of the reaction was raised to 22° C., and the reaction was stirred at this temperature for one day.

On the 23$^{rd}$ day, 1020 mL of distilled trifluoromethanesulfonic acid was added, and the temperature of the reaction was raised to 25° C. The mixture was stirred at this temperature overnight. Following this, the mixture (containing suspended precipitate) was transferred to a 5-liter, three neck, round-bottom flask and was heated to 40° C. without stirring. The mixture was allowed to stand at this temperature for five days. At the end of five days, the temperature of the reaction was lowered to 0° C. overnight. The next day, 120 mL of 98-100% nitric acid ($HNO_3$) was added dropwise with agitation of the mixture, which was then allowed to stand without stirring for four days.

The resulting precipitate was filtered on a coarse sintered glass funnel, washed with 98-100% $HNO_3$, followed by water, followed by 10% aqueous potassium bicarbonate ($KHCO_3$) solution, followed by more water, and then air-dried to yield 22.02 g (0.054 mole) of effectively pure HNFX. Nitric acid (100 ml of 98-100% $HNO_3$) was added dropwise to the crude reaction filtrate, with stirring, and the mixture was stirred overnight at ambient temperature. The following day, there was no more precipitate visible, so the mixture was poured over approximately 3 L of ice-water with agitation. The resulting precipitate was filtered on a coarse sintered glass funnel and washed with water to yield 19.58 g (approximately 0.048 mole) of crude HNFX.

Example 4

One-Pot Difluoramination/Denosylation/Nitration

To a 4-liter jacketed cylindrical flask (the "reactor"), which had been previously purged with nitrogen for 1 hour, was added 590 mL of fuming sulfuric acid (20% $SO_3$) and 1180 mL of trichlorofluoromethane ("Freon"). The flask was equipped with a mechanical stirrer, a Dewar-style reflux condenser (containing dry ice, acetone, and a refrigerated cold-finger), and an inert-oil-filled bubbler. The fuming sulfuric acid-Freon mixture was cooled with a chilled circulating bath. To a separate 5-liter, 3 neck, round-bottom flask was added 3 liters of aqueous N,N-difluorourea solution containing 7.6 moles difluorourea. When the difluoramination reactor temperature reached <5° C., gaseous difluoramine ($HNF_2$) was generated from the difluorourea solution by acidic hydrolysis with sulfuric acid, as described by Parker and Freeman [*Inorganic Syntheses* 1970, 12, 307], and absorbed into the cooled fuming sulfuric acid. When $HNF_2$ generation was complete (and the reactor had cooled further), tetrahydro-1,5-bis(4-nitrobenzenesulfonyl)-1,5-diazocine-3,7(2H,6H)-dione A (150 g, 0.293 mole) was added to the fuming sulfuric acid-Freon mixture, the reactor flask was sealed and cooled further to −25° C., and the mixture was stirred.

On the 6$^{th}$ day of reaction, 155 mL of fuming sulfuric acid (30% $SO_3$) was added over two hours while keeping the temperature of the reaction at −8° C. The reaction flask was then sealed, and the contents were stirred at −11° C. for two days.

On the 8$^{th}$ day, the reaction mixture was transferred to a 5-liter, three neck, round-bottom flask and the temperature was increased (with mechanical stirring maintained) to 25° C. for four hours to drive off excess $HNF_2$ and Freon. Distilled trifluoromethanesulfonic acid (1500 mL) was added dropwise with stirring, and the mixture was stirred at 25° C. for three days. On the 11$^{th}$ day, the temperature of the reaction was increased to 40° C., and the reaction mixture was stirred at this temperature for nine days.

On the 20$^{th}$ day, the mixture was cooled to 5° C., and 120 mL of 98-100% nitric acid ($HNO_3$) was added dropwise while stirring. The cooling bath's temperature was set at 20° C., and the reaction mixture was stirred overnight. The next morning, the resulting precipitate was filtered on a medium-porosity sintered glass funnel and then washed with 98-100% $HNO_3$ and then water, followed by 10% aqueous potassium bicarbonate ($KHCO_3$) solution and then water. The solid was dried in a vacuum oven, yielding effectively pure HNFX, confirmed by NMR analysis (30.99 g, 0.076 mole).

Nitric acid (120 mL of 98-100% $HNO_3$) was added to the crude reaction filtrate while stirring and cooling it in an ice bath. The bath was replaced with a water bath, and the mixture was stirred overnight. On quenching onto ice the next day, followed by similar washing as above, additional crude HNFX (6.48 g, approximately 0.016 mole) was recovered.

In the successful examples cited above, 4-nitrobenzenesulfonyl (nosyl) was used as a model nitrogen-protecting sulfonyl group to prepare electronegatively substituted diazocines suitable as intermediates and precursors leading to geminal-bis(difluoramino)alkylene derivatives. A variety of other heretofore unknown tetrahydro-1,5-diazocine-3,7(2H, 6H)-dione derivatives suitable for conversion to geminal-bis (difluoramino)alkylene derivatives become apparent from a review of known electron-withdrawing properties of sulfonyl substituents, such as reviewed by Hansch et al. (op. cit.). These require that inductive substituent constants, $\rho_I$ or F, are greater than approximately 0.58, the value known for unsubstituted benzenesulfonyl. Thus, other suitable electronegatively substituted diazocines include those protected on nitrogen by chlorosulfonyl; fluorosulfonyl; cyanosulfonyl; polyhaloalkanesulfonyls, including difluoromethanesulfonyl, trifluoro-methanesulfonyl, and all perfluoroalkanesulfonyls; arenesulfonyls appropriately substituted such that collective effects of substituents on the arene impart the desired electronegativity to the arenesulfonyl, including, but not limited to, nitrobenzenesulfonyl (any isomer) and all polynitrobenzenesulfonyls. Arenesulfonyl substituents may be based on arenes other than benzene, including various aromatic heterocycles, including azines. Individual substituents on the arenesulfonyl of electronegativity comparable to or greater than that of nitro impart suitable electronegativity to the sulfonyl substituent to make suitable diazocine intermediates. The collective effect of multiple electronegative substituents of electronegativity less than that of nitro would also impart, collectively, the same necessary property of lowered basicity; examples include polyhaloarenesulfonyl and polycyanoarenesulfonyl protecting groups; other examples are apparent from compilations of quantitative inductive substituent effects, such as Hansch et al. (op. cit.).

Difluoramination of ketones like tetrahydro-1,5-bis(4-nitrobenzenesulfonyl)-1,5-diazocine-3,7(2H,6H)-dione (A) has been demonstrated to proceed in a wide range of temperatures, including −25 to +40° C., but the preferred temperature range is −25 to 0° C. for convenience in spectroscopically monitoring the progress of difluoranination and commencement of competitive protolytic N-denosylation. At a temperature of +15° C., for example, the difluoramination requires only about 2 days; but monitoring of its progress should then be conducted more frequently in the latter stage of the reaction. For temperatures above approximately 20° C., an alternative inert solvent besides trichlorofluoromethane (b.p. 21° C.) should be used. For reactions of shorter duration, other suitable solvents are apparent for higher-temperature use, including numerous unreactive hydrohalocarbons (such as dichloromethane) and chlorofluorocarbons.

In the successful examples cited above, trifluoromethanesulfonic acid was employed as an ideal superacid for effecting protolytic denosylation of the protected diazocine intermediate(s). Numerous other superacids stronger than sulfuric acid, such as those reviewed by Olah et al. (op. cit.), would be suitable for effecting protolytic denosylation of N-alkylnosylamide derivatives. Even fuming sulfuric acid ($H_2SO_4$—$SO_3$) is capable of doing so, but that system offers a disadvantage that it may perform as an oxidizing or sulfonating reagent (toward certain reactants) in competition with protolysis. The system of difluorosulfamic acid-sulfuric acid, which is formed upon reaction of $HNF_2$ with $SO_3$ contained in fuming sulfuric acid, is also sufficiently strong to effect protolytic denosylation of 3,3,7,7-tetrakis(difluoramino)octahydro-1, 5-bis(4-nitrobenzenesulfonyl)-1,5-diazocine (B), which is eventually observed (spectroscopically) as a side reaction in competition with difluoramination of tetrahydro-1,5-bis(4-nitrobenzenesulfonyl)-1,5-diazocine-3,7(2H,6H)-dione (A where R=4-nitrophenyl). Thus, difluoramination may be followed by in-situ denosylation with the acid mixture (difluorosulfamic acid-sulfuric acid) used for difluoramination.

A disadvantage of that system is that the solubility of the 3,3,7,7-tetrakis(difluoramino)octahydro-1,5-bis(4-nitrobenzenesulfonyl)-1,5-diazocine (B) reactant in that mixture is low, so the process of denosylation is slower than when a superior superacidic cosolvent is added. Trifluoromethanesulfonic acid is such a superior superacidic cosolvent in which organic reactants like 3,3,7,7-tetrakis(difluoramino) octahydro-1,5-bis(4-nitrobenzenesulfonyl)-1,5-diazocine (B) are more soluble. Other attractive superacids for this purpose would include fluorosulfonic acid, any perfluoroalkanesulfonic acid, and any perfluoroarenesulfonic acid. Such individual superacids may be made even stronger by adding appropriate good Lewis acids, including antimony pentafluoride or bismuth trifluoromethanesulfonate, so such combinations are also suitable for effecting protolytic denosylation. Superacids would be capable of protolytically deprotecting diazocines protected with alternative N-protecting groups besides nosyl (as suggested above), which would also produce the desired 3,3,7,7-tetrakis(difluoramino)octahydro-1,5-diazocinium salt (C).

In the successful examples cited above, nitric acid was employed as a nitrating reagent. Any other electrophilic nitrating species may be used instead, including any nitronium salt. Electrophilic nitrating compounds and systems suitable for nitration are reviewed by Olah et al. ["Nitration: Methods and Mechanisms," VCH Publishers, 1989]. Nitrate esters or nitrate salts placed in the presence of superacids used for protolytic denosylation would also form nitronium equivalents capable of nitrating diazocinium intermediate(s) to HNFX. More-dilute aqueous solutions of nitric acid that are still electrophilic nitrating reagents (such as 70-90% $HNO_3$) would be suitable for nitrating deprotected diazocinium intermediates.

Applications of the present invention particularly include use as precursor(s) to HNFX (useful in rocket propellants and explosives) as well as to other members of the rare class of 3,3,7,7-tetrakis(difluoramino)octahydro-1,5-diazocines. The calculated performance improvements expected from geminal-bis(difluoramino)-substituted heterocyclic nitramines, such as HNFX, when formulated into explosives and propellants have been reported by Miller [*Materials Research Society Proceedings* 1996, 418, 3].

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:

1. A process for preparing 3,3,7,7-tetrakis(difluoramino) octahydro-1,5-diazocinium salt of the structure (C) comprising:

providing a tetrahydro-1,5-disulfonyl-1,5-diazocine-3,7 (2H,6H)-dione of the structure (A)

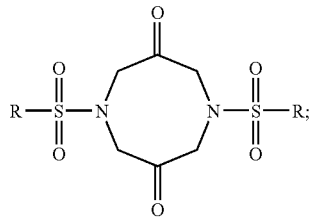

(A)

reacting said tetrahydro-1,5-disulfonyl-1,5-diazocine-3,7 (2H,6H)-dione with a difluoraminating acid selected from the group consisting of a mixture of difluoramine and difluorosulfamic acid in sulfuric acid, a difluorosulfamic acid-sulfuric acid mixture, a fluorosulfonic acid, a perfluoroalkanesulfonic acid, and a perfluoroarenesulfonic acid, to form a first mixture of reaction products one of which has the structure (B)

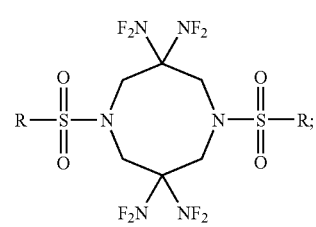

(B)

and reacting said first mixture with a superacid free of nitrating species and having a $H_0$ less than or about −11 to form a second mixture of reaction products one of which has the structure (C)

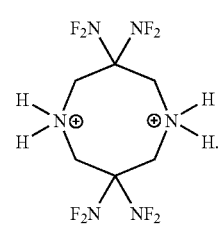

(C)

2. The process of claim 1 further comprising combining said second mixture of reaction products with a nitrating species to form a third mixture of reaction products including the nitramine 3,3,7,7-tetrakis(difluoramino)octahydro-1,5-dinitro-1,5-diazocine.

3. A process for preparing 3,3,7,7-tetrakis(difluoramino) octahydro-1,5-diazocinium salt (C) comprising:
    mixing a selected inert solvent and a selected superacid free of nitrating species and having an $H_0$ less than or about −11 to form a first mixture;
    dissolving difluoramine ($HNF_2$) in said first mixture at about 0° C. to about +9° C. to form a first composition;
    cooling said first composition to about −8° C.;
    adding tetrahydro-1,5-bis(4-nitrobenzenesulfonyl)-1,5-diazocine 3,7(2H,6H)-dione to said first composition to form a second composition;
    stirring said second composition for a predetermined time at about −25° C. to about 0° C., allowing contact of reactants, to form a third composition;
    stirring a third composition at about +20° C. to about +25° C., until excess inert solvent and $HNF_2$ have substantially been removed, to form a fourth composition;
    adding trifluoromethanesulfonic acid to said fourth composition to form a fifth composition;
    stirring said fifth composition for a predetermined time at about +25° C., allowing contact reactants, to form a sixth composition; and
    stirring said sixth composition for a predetermined time at about +40° C., allowing contact of reactants, to form a seventh composition containing a 3,3,7,7-tetrakis(difluoramino)octahydro-1,5-diazocinium salt.

4. The process of claim 3 wherein said inert solvent is trichlorofluoromethane, dichloromethane, an unreactive hydrohalocarbon, an unreactive chlorofluorocarbon, or a combination thereof.

5. The process of claim 3 wherein said superacid is fuming sulfuric acid, difluorosulfamic acid-sulfuric acid, trifluoromethanesulfonic acid, fluorosulfonic acid, a perfluoroalkanesulfonic acid, a perfluoroarenesulfonic acid, or a combination thereof.

* * * * *